(12) United States Patent
Cline et al.

(10) Patent No.: US 8,451,314 B1
(45) Date of Patent: May 28, 2013

(54) BI-DIRECTIONAL COMMUNICATION SYSTEM

(75) Inventors: Chris Cline, Smithville, MO (US);
James Monroe, Shawnee, KS (US);
Todd Bechtel, Overland Park, KS (US);
Jerry Jeffress, Plano, TX (US)

(73) Assignee: Cerner Innovation, Inc., Lenexa, KS (US)

( * ) Notice: Subject to any disclaimer, the term of this patent is extended or adjusted under 35 U.S.C. 154(b) by 265 days.

(21) Appl. No.: 12/950,744

(22) Filed: Nov. 19, 2010

Related U.S. Application Data

(60) Provisional application No. 61/281,732, filed on Nov. 20, 2009.

(51) Int. Cl.
*H04N 7/15* (2006.01)

(52) U.S. Cl.
USPC .................. 348/14.08; 348/14.05; 348/14.09; 348/14.12

(58) Field of Classification Search
USPC ............................ 348/14.01–14.16; 600/300
See application file for complete search history.

(56) References Cited

U.S. PATENT DOCUMENTS

| 6,094,221 A * | 7/2000 | Andersion ................. 348/231.6 |
| 2004/0121729 A1 * | 6/2004 | Herndon et al. ............. 455/12.1 |
| 2007/0271122 A1 * | 11/2007 | Zaleski .............................. 705/3 |

FOREIGN PATENT DOCUMENTS

WO    WO 9407327 A1 *  3/1994

* cited by examiner

*Primary Examiner* — Melur Ramakrishnaiah
(74) *Attorney, Agent, or Firm* — Shook, Hardy & Bacon L.L.P.

(57) ABSTRACT

Methods, computer systems, and computer readable media for one way and two way video and audio communications between a clinician at a remote location and a patient located in a patient room that is in a location different from the clinician are provided.

16 Claims, 5 Drawing Sheets

BI-DIRECTIONAL COMMUNICATION SYSTEM

CROSS REFERENCE TO RELATED APPLICATIONS

This application claims the benefit of, and expressly incorporates by reference, U.S. Provisional Application No. 61/281,732, filed on Nov. 20, 2009.

BACKGROUND

Patients in a healthcare environment, including critically ill patients, may have their care supplemented by a clinician at a remote location. The clinician at the remote location can view a patient at a healthcare facility that is different from the location of the clinician.

BRIEF DESCRIPTION OF THE DRAWINGS

Embodiments are described in detail below with reference to the attached drawing figures, wherein.

DETAILED DESCRIPTION

Figure 1:
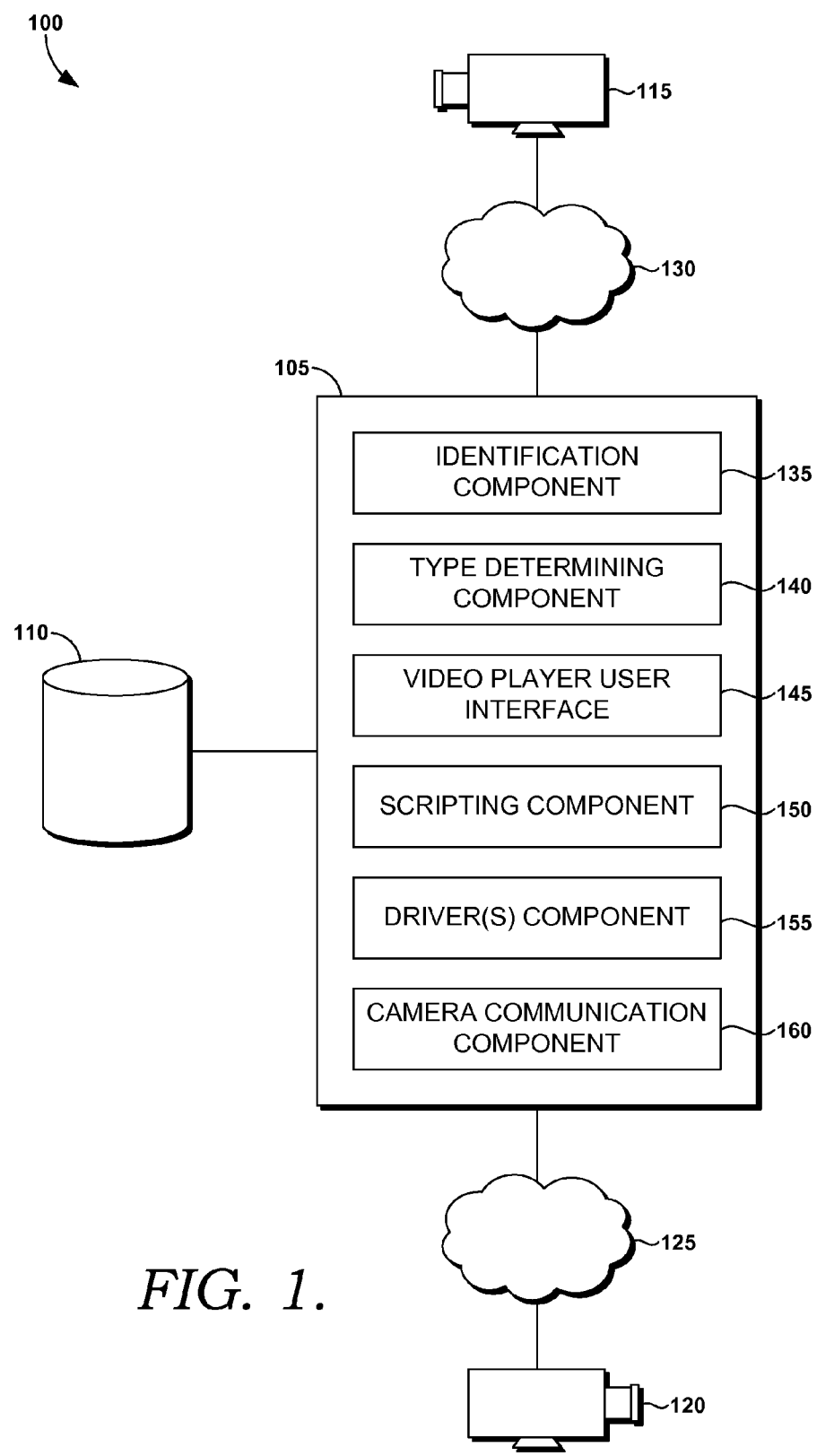
FIG. 1 is a block diagram of an exemplary computing environment suitable to implement embodiments of the present invention.

Embodiments of the present invention are directed to methods, computer systems, and computer readable media for one way and two way video communications between a clinician at a remote location and a patient located in a patient room that is in a location different from the clinician.

Having briefly described embodiments of the present invention, an exemplary operating environment suitable for use in implementing embodiments of the present invention is described below. An exemplary computing environment (e.g., medical-information computing-system environment) with which embodiments of the present invention may be implemented is described and is merely an example of one suitable computing environment and is not intended to suggest any limitation as to the scope of use or functionality of the invention. Neither should the computing environment be interpreted as having any dependency or requirement relating to any single component or combination of components described therein.

The present invention might be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules include routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

The computing environment includes at least one general purpose computing device in the form of a control server. Exemplary components of the control server include a processing unit, internal system memory, and a suitable system bus for coupling various system components, including database cluster, with the control server. The system bus might be any of several types of bus structures, including a memory bus or memory controller, a peripheral bus, and a local bus, using any of a variety of bus architectures. Exemplary architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server typically includes therein, or has access to, a variety of computer-readable media, for instance, database cluster. Computer-readable media can be any available media that might be accessed by server, and includes volatile and nonvolatile media, as well as, removable and nonremovable media. Computer-readable media might include computer storage media. Computer storage media includes volatile and nonvolatile media, as well as, removable and nonremovable media implemented in any method or technology for storage of information, such as computer-readable instructions, data structures, program modules, or other data. In this regard, computer storage media might include RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server. Combinations of any of the above also may be included within the scope of computer-readable media.

The computer storage media discussed above, including database cluster, may store computer-readable instructions, data structures, program modules, program components and other data.

The control server might operate in a computer network using logical connections to one or more remote computers and other remote hardware devices such as cameras, speakers, microphones and monitors. Remote computers and hardware devices might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians might include a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers and hardware devices might also be physically located in nontraditional medical care environments so that the entire healthcare community might be capable of integration on the network. The remote computers might be personal computers, servers, routers, network PCs, peer devices, other common network nodes, or the like and might include some or all of the elements described above in relation to the control server. The devices can be personal digital assistants or other like devices.

Exemplary computer networks include local area networks (LANs) and/or wide area networks (WANs). Such networking environments are commonplace in offices, enterprise-wide computer networks, intranets, and the Internet. When utilized in a WAN networking environment, the control server might include a modem or other means for establishing communications over the WAN, such as the Internet. In a networked environment, program modules or portions thereof might be stored in association with the control server, the database cluster, or any of the remote computers. For example, various application programs may reside on the memory associated with any one or more of the remote computers. It will be appreciated by those of ordinary skill in the art that the network connections shown are exemplary and other means of establishing a communications link between the computers (e.g., control server and remote computers) might be utilized.

In operation, a clinician might enter commands and information into the control server or convey the commands and information to the control server via one or more of the remote computers through input devices, such as a keyboard, a pointing device (commonly referred to as a mouse), a trackball, or a touch pad. Other input devices include microphones, satellite dishes, scanners, or the like. Commands and information might also be sent directly from a remote healthcare device to the control server. In addition to a monitor, the control server and/or remote computers might include other peripheral output devices, such as speakers and a printer.

Although many other internal components of the control server and the remote computers are not shown, those of ordinary skill in the art will appreciate that such components and their interconnection are well known. Accordingly, additional details concerning the internal construction of the control server and the remote computers are not further disclosed herein.

Turning now to FIG. 1, the schematic diagram depicts an operating environment, identified generally by reference number numeral 100, suitable to practice an embodiment of the present invention. FIG. 1 includes various components that communicate with one another including a video communication manager 105, patient records 110, camera hardware devices 115 and 120. Before describing in detail how these components communicate, each component will be described generally.

In an embodiment of the present invention, camera hardware devices 115 and 120 may be the same type of camera hardware device or may be different camera hardware devices. In one embodiment, camera hardware device 115 is located at a remote location of a clinician. In this embodiment, the camera hardware device 120 is located at a patient location, such as at the patient's home or room of a healthcare facility. Exemplary camera hardware devices including, but are not limited to, Internet Protocol (IP) based cameras, Sony PCS Cameras, and Axis 24001 Cameras. It will be appreciated that any type of video camera and associated driver may be utilized in embodiments of the present invention. In particular, video communication manager 105 allows for communication and use of any type of video camera hardware device and is hardware agnostic. The video communication manager 105 provides the capability to support a variety of cameras depending on the needs of the facility.

Patient records 110 include electronic medical records for patients (also referred to herein as "EMR"). EMRs include an electronic version of patient records including information for the patient such as medication and infusion orders, tasks, images, examination reports, testing and lab results, medical history, patient demographic information, and the like. Patient records 110 may also include orders and tasks to be completed for a particular patient.

Video communication manager 105 is in communication with patient records 110, camera hardware devices 115 and 120. Video communication manager 105 includes an identification component 135, a type determining component 140, a video player user interface component 145, a scripting component 150, a driver component 155, and a camera communication component 160. While these components are included in the embodiment of FIG. 1, any number of components either more or less than the illustrated components, may be used to accomplish the purposes of the present invention. Other components and subcomponents are contemplated to be within the scope of the present invention. Furthermore, although depicted as residing on one device, such as a server or personal computing device, it will be appreciated that any number of components and/or subcomponents may reside on any number of computing devices or servers.

Identification component 135 receives an identification of a patient and/or a patient room for which a clinician located at a remote location would like to contact. On one embodiment, for example, if a clinician at a remote location is looking at patient records for a particular patient, the clinician may request to initiate a contact and video link with the patient and/or the patient's room. In another embodiment, the clinician may enter a patient identification number, patient name and/or a patient room number and request initiation of a video link with the identified patient or patient room. It will be appreciated that the identifications may be received in any variety of ways, including, but not limited to, selection of a patient or patient room by a clinician at a remote location from a user interface, manual or textual entry of patient information and/or patient room information or scanning of a bar code associated with the patient and/or patient room.

Type determining component 140 determines the information for the camera that is located in the identified patient's room. This information includes IP address and the type of driver utilized for communication with the camera. For example, if a clinician would like to contact patient Annie Oakley, a request for a video link is made by the remote clinician. Type determining component 140 determines the IP address, camera and type of driver for the camera located in the patient room for Annie Oakley. This may be done by accessing a database or XML table listing the hardware devices such as cameras, drivers, and IP addresses for the patient room camera associated with each patient room. If the patient has only been identified by name, another database may be accessed to determine the patient location or patient room for which the patient has been assigned. For example, one patient room in a facility may contain an IP camera, while another patient room in the same facility may contain a Sony video camera. This information would be stored in the database or XML table that may be accessed by the type determining component 140 upon identification of the patient or patient room by identification component 135.

Figure 4:
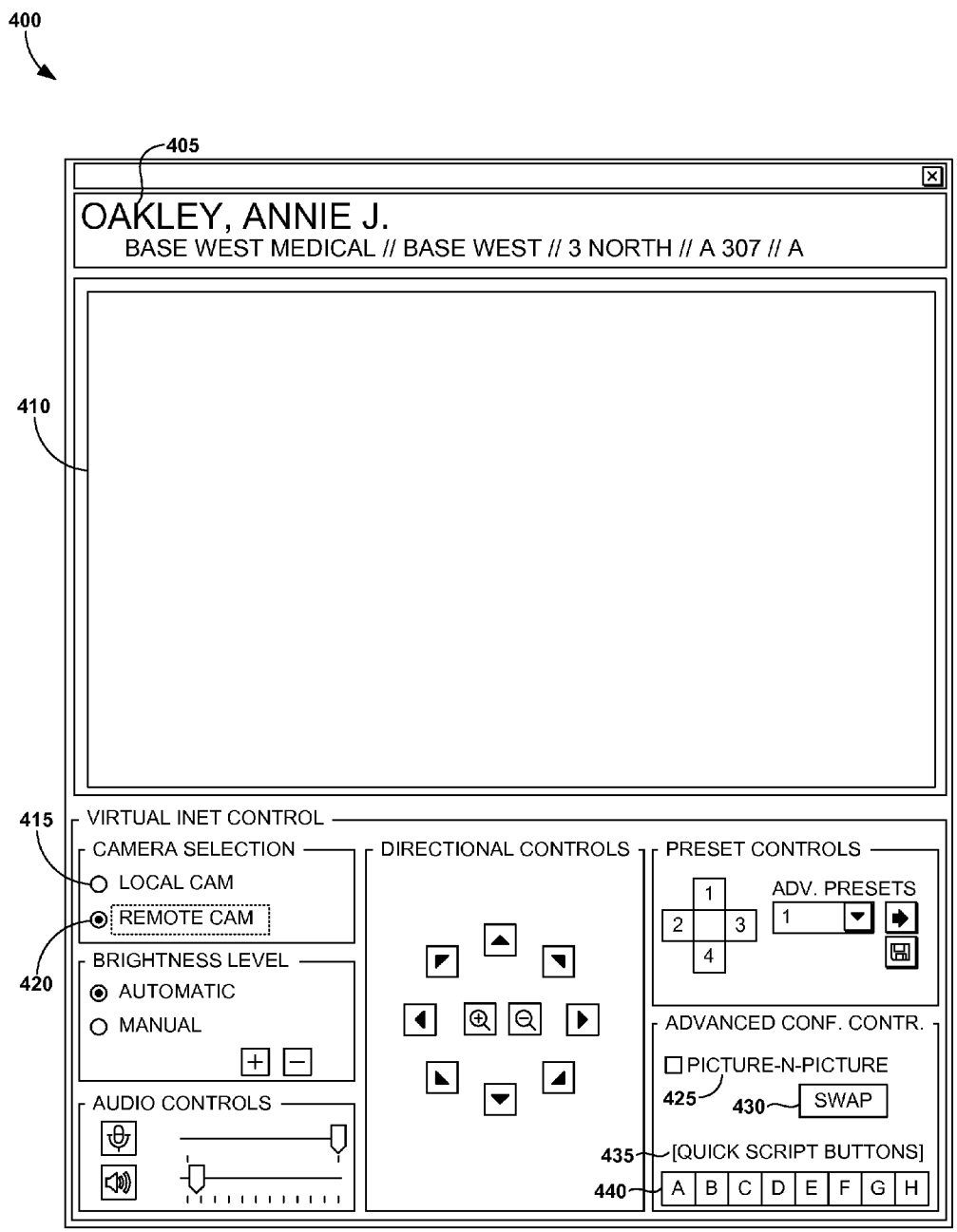
FIG. 4 is a screen shot of a graphical user interface that may be utilized in accordance with embodiments of the present invention.

Video player user interface component 145 displays a generic user interface to the remote clinician. The generic user interface may be utilized for communication with any type camera that may be located in a patient's room that the clinician at a remote location would like to view. Such an exemplary user interface is shown in FIG. 4. The user interface is hardware agnostic and may be utilized to view video received from any type of camera from a patient room. In addition, the user interface may be utilized to manipulate any type camera in the patient room or at the remote location of the clinician.

Scripting component 150 includes generic scripts that may be utilized to operate any type camera and other hardware devices at the patient location or clinician location. There are four different types of scripts utilized by scripting component 150. Each type of scripting allows scripting to occur for the camera hardware device at different times. Startup scripting may occur before a remote connection has been established between the clinician at a remote location and with the hardware camera device at the patient location. This scripting would allow for various player or local camera settings to be established prior to connection. This could include things such as muting a microphone located at the remote clinician site, ensuring any camera device at the remote clinician location is centered to a default location and scripting to default local speaker volumes at the remote clinician location. Connection scripting occurs following establishment of a remote connection between a clinician at a remote location and a patient room at a different location. The connection scripting may include sending default settings to the remove camera device or other hardware devices such as microphones, speakers, and monitors at the patient's room location. The connection scripting may include things such as aiming the camera hardware device at the patient, ensuring that the microphone at the patient location is not muted and making sure the speakers are on at the patient location.

Shutdown scripting may incur at the time immediately prior to disconnection of the remote connection between the clinician at the remote location in the patient room. Exemplary scripting that may occur for shutdown includes facing the remote camera at the patient location away from the patient, and turning off any speakers or microphones. On demand scripting may be utilized by an end user, such as a clinician at a remote location to perform particular scripts during the session. For example, instead of having to zoom in multiple times to see a patient, a script button may be provided in a user interface to the clinician such that it automatically zooms the camera hardware device five times by pressing one button. Other scripting that may be utilized on demand include enabling or disabling night vision of a camera hardware device, performing manual focusing, informing a remote camera device to perform various other functions such as establishing a remote connection to another camera, such as a camera located at the clinician's remote location. On demand script buttons are displayed in FIG. 4.

It will be appreciated that any variety of scripting may be utilized including, but not limited to enabling auto brightness of a camera hardware device, disabling auto brightness of a camera hardware device, increasing brightness, decreasing brightness, selecting a near camera in the instance where there are more than one camera hardware devices at a location, selecting a camera for when there are multiple camera hardware devices at a location, panning a camera to the left or right, tilting the camera up or down, tilting the camera diagonally up and left, up and right, down and left, and down and right. Additional scripting may be done to zoom a camera device in, zoom a camera device out, muting a local microphone and unmuting a local microphone, muting a speaker, or unmuting a speaker and moving a camera to a designated present. Additional scripting may be done for remote control buttons if the camera has a remote control, enabling picture and picture or disabling picture and picture, setting speaker and microphone volumes at both patient room location and the remote location of the clinician.

It will be appreciated that video communication manager 105 may include multiple driver components 155 for multiple camera hardware devices. Driver components 155 allow for the scripting functionality described above to be converted into the proper driver commands for different types of camera hardware devices. For example, if a healthcare facility had three different types of camera hardware devices in different patient rooms, the video communication manager 105 includes driver components for the three different hardware camera devices. Each driver converts the scripting functionality into hardware specific commands to communicate with the camera hardware device such that it would perform the requested actions. For example, scripting functionality to tilt a camera up, may require a different command for each driver for each hardware device. For example, the tilt up command for a IP camera may be the command "UP" while the driver command for a Sony camera may be "TILTUP." The driver would convert the scripting functionality to the proper commands based on the type of driver and camera hardware device that is determined by type determining component 140.

Camera communication component 160 communicates the driver commands of driver component 155 to camera hardware devices 115 and 120. It will be appreciated that these driver commands may be communicated via networks 125 or 130. Exemplary communications protocols that may be utilized by camera communication components include Winsock Protocol, Transporters and WinInet Protocol Transporters. It will be appreciated that any variety of communication methods may be utilized to communicate the commands to the hardware devices located at the patient location and the clinician remote location.

Figure 2:
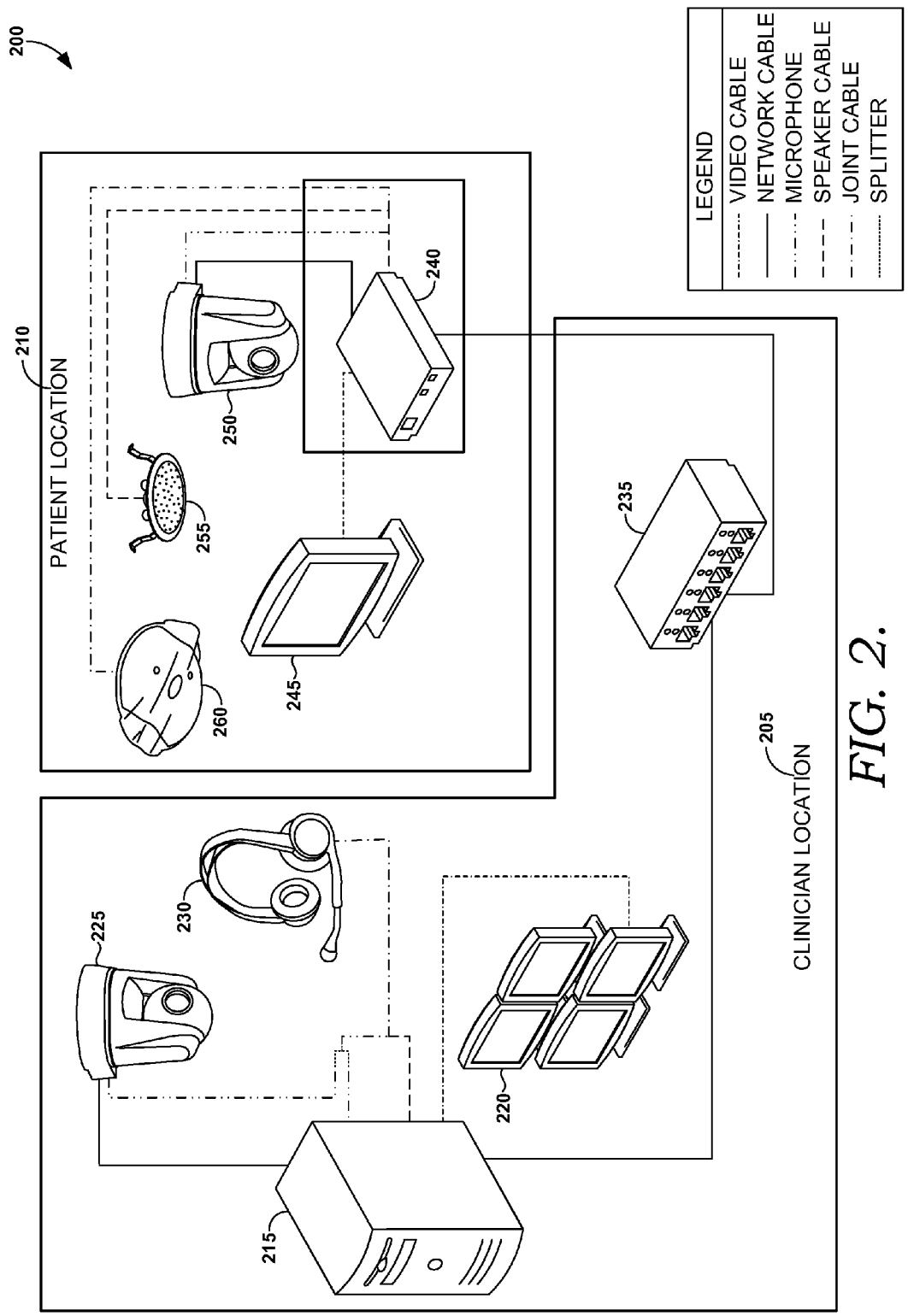
FIG. 2 is an exemplary system architecture suitable to implement embodiments of the present invention.

Turning now to FIG. 2, a schematic diagram depicts an exemplary hardware device configuration located at both a remote clinician location 205 and a patient location 210. At the clinician location, there may be a server 215 (in one embodiment, the communication manager 105 resides on server 215) a camera hardware device 225, a speaker and microphone combination 230, and monitors 220 for viewing video from the patient location and graphical user interfaces. The information from these devices and from video communication manager 105 may be communicated via a network communication hardware device 235.

At the patient location 210, there may be a network device 240, a monitor 245 for viewing information and video from the clinician remote location, a camera hardware device 250, a speaker 255 for listening to audio from the clinician location 225 and a microphone 260 for input of audio information to communicate from the patient location 210 to the clinician location 205.

Figure 3A:
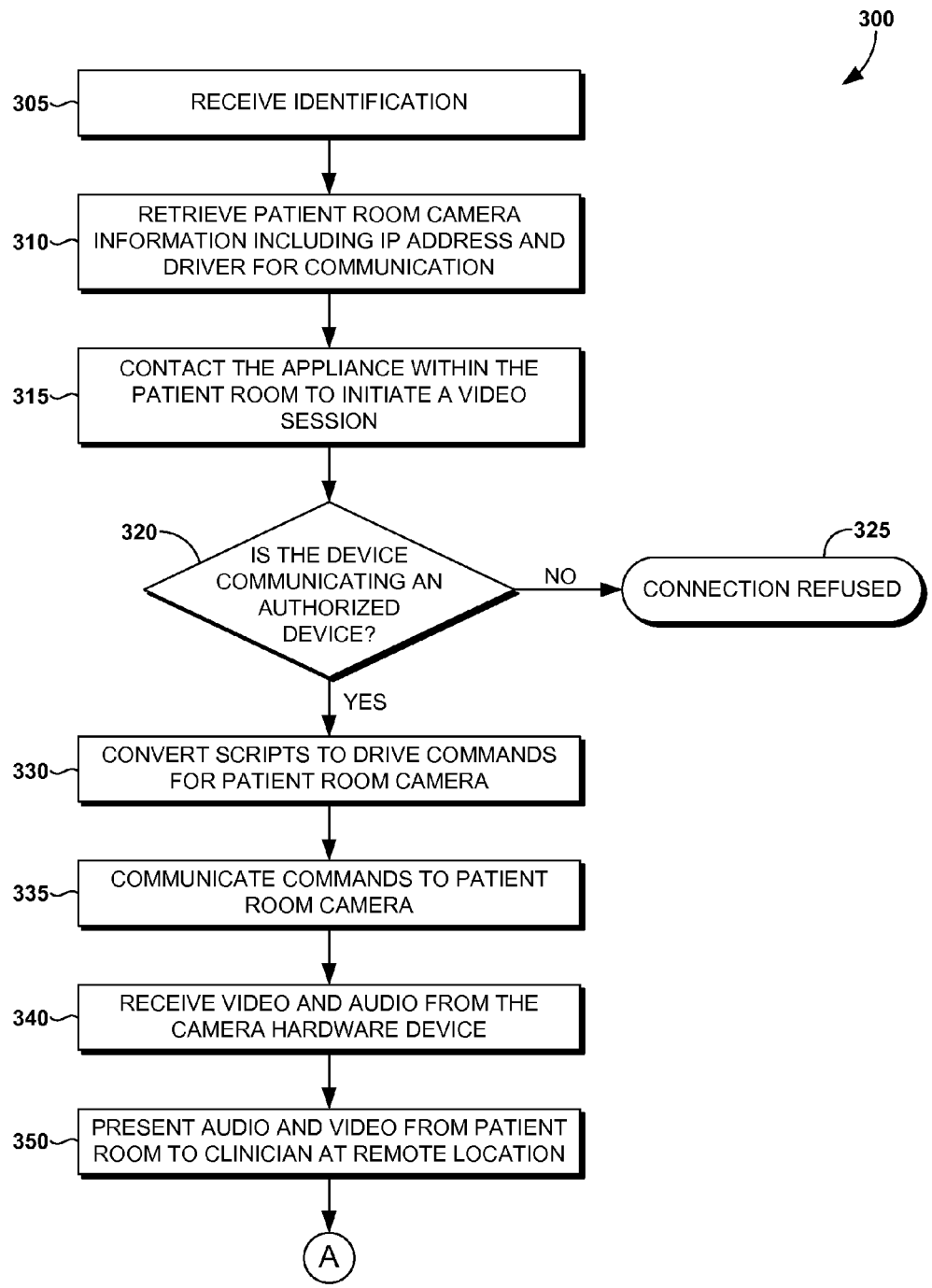
FIGS. 3A and 3B depict a flow diagram of a method performed in accordance with embodiments of the present invention.
Figure 3B:
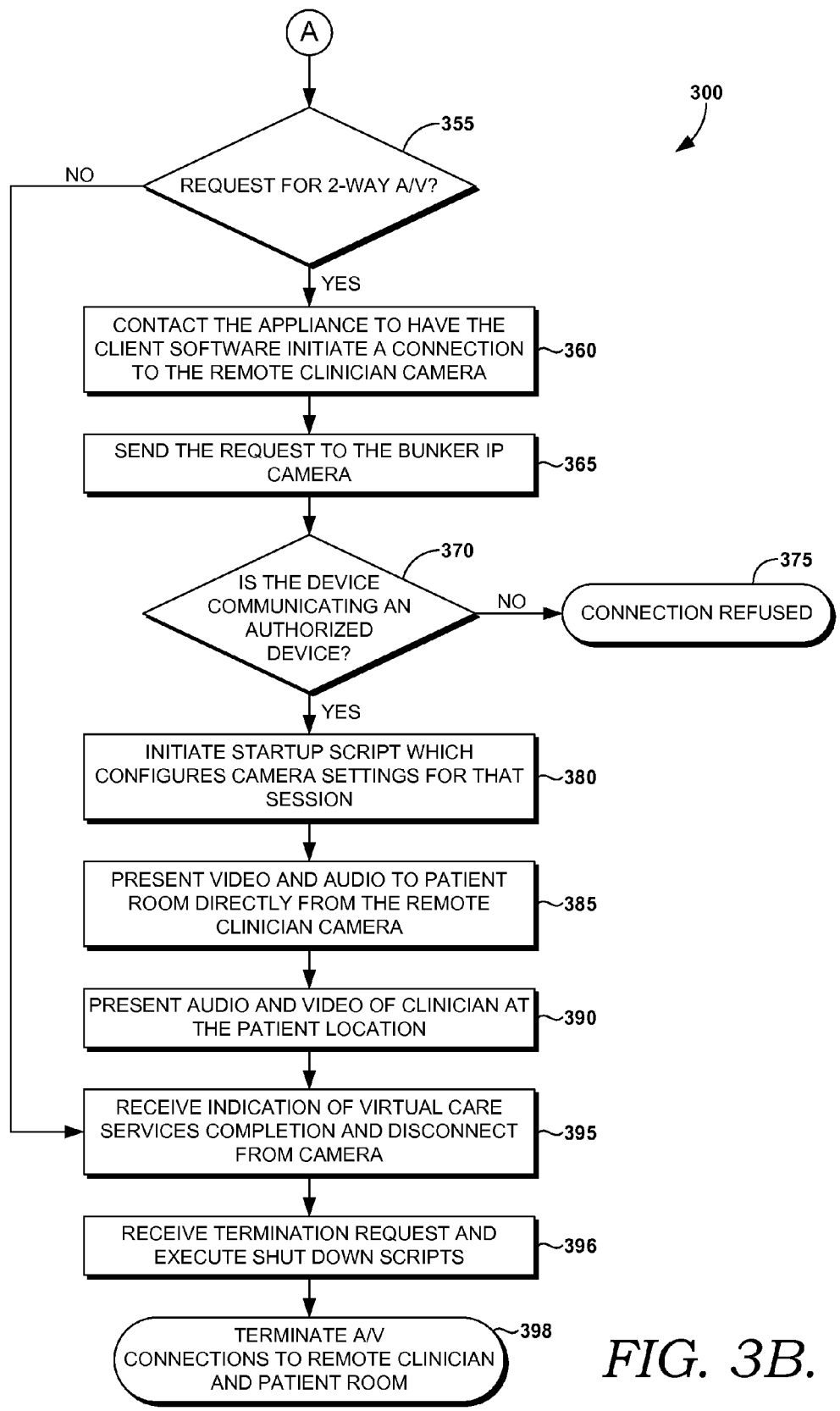

With reference to FIGS. 3A and 3B, an illustrative flow diagram 300 is shown of a method for communicating and transmitting video between a remote clinician location and a patient room location. At step 305, identification of a patient or patient room is received from a clinician. For example, the clinician may make a request from a patient record application, such as Cerner Millennium, or another application to contact a patient room located at a location different from the clinician.

At step 310, information relating to the camera hardware device located in the identified patient's room including the IP address and driver for communication is determined. At step 315, the video communication manager contacts the camera hardware device within the patient's room to initiate a video session. This may be done by sending a communications signal via a network from the clinician remote location to the patient room. At step 320, it is determined whether the devices communicating are authorized devices. If the devices are not authorized to communicate, the connection is refused at step 325.

If the devices are authorized to communicate at step 330, start up scripts that initiate and configure camera settings and other hardware at the patient location are initiated. At step 335, the scripts are converted into driver commands that are associated with the type of camera device in the patient room. Next step, step 340, the driver device commands are communicated to the hardware camera device in the patient room. At step 345, video and audio from the camera hardware device at the patient room location is received. At step 350, the audio and video from the patient room is presented to a clinician at the remote location. For example, the audio and video information from the patient room may be displayed on monitor 220 of FIG. 2.

At step 355, it is determined whether there has been are request received for two-way audio visual communication by the clinician. If not, the system proceeds to step 395. If there has been a request at 355 for two-way audio/visual communication at step 360, the video communication manager 105 contacts the camera hardware device at the remote clinician location. At step 365, the request is sent to the IP hardware camera device at the location. At step 370, it is determined whether the devices communicating are authorized to communicate. If not, at 375, the connection is refused.

If at step 370, it is determined that they are authorized to communicate at step 380, startup scripts are initiated to configure the camera hardware device at the clinician's remote location. Exemplary camera at the clinician's remote location is depicted in 225 of FIG. 2. At step 385, the video and audio from the remote clinician camera 225 is sent to the patient room and may be displayed on exemplary monitor 245 at the patient room location. At step 395, an indication is received from the clinician that the virtual care services are completed and to disconnect the one or more connected cameras. At step 396, a request is received and any shutdown scripts are executed. These scripts are converted to driver commands and sent to the appropriate camera hardware devices to perform the shutdown functions. At step 398, the connections to one or more of the remote clinician and patient room camera devices are terminated.

In one embodiment, video and audio is directly streamed from the clinician's remote location camera and microphone to the patient room monitor while video and audio is simultaneously and directly streamed from the patient's location camera and microphone to one or more monitors at the clinician's remote location. It will be appreciated that the delay for the direct streaming is minimal and/or is similar to that experienced using codec or other processing. In one embodiment, the video and audio is streamed directly from the patient's location to the remote clinician's location or vice versa without the use of codec or other encoding of the data streams. A codec encodes a data stream or signal for transmission, storage or encryption, or decodes it for playback or editing.

With reference to FIG. 4, an illustrative graphical user interface 400 is shown of a generic graphical user interface for video communication with any type of camera hardware device. The interface 400 includes identification of the patient and/or patient location 405. The user interface includes an area for displaying video from the patient room location on the screen located at the clinician's remote location 410. The graphical user interface further includes buttons to allow a clinician to choose whether or not to view a local camera at 415 at the clinician's remote location or at the clinician location or a remote camera 420 that is located in patient's room. This selection would determine which video is displayed in video section 410. In addition, the graphical user interface 400 includes buttons to allow the clinician to swap 430 between video feed from the patient room location and from the clinician's location. For example, the clinician may have a large screen of the clinician's location video and a smaller picture and picture screen of the patient's room location while the clinician is adjusting the camera settings at the clinician's location. Once the clinician has determined that the camera at the clinician location is properly configured, the clinician may select a picture and pictures swap such that now the video from the patient room is the larger area in space 410. Graphical user interface 400 also includes quick script buttons 440 that may be selected by the clinician in order to perform quick adjustments to the one or more camera hardware devices located at the patient room or the clinician's location.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. One or more computer-readable storage media having computer-executable instructions embodied thereon, that, when executed by a computing device, executes driver commands for a camera hardware device in a patient's room, the method comprising:

receiving a request from a clinician to establish contact with a patient at a separate patient location, wherein the request is received from an electronic medical record for the patient while the clinician is accessing the electronic medical record;

receiving identification of a patient location having a camera hardware device;

determining a driver for the camera hardware device in the patient's location;

connecting with the camera hardware device;

receiving one or more script requests to execute one or more scripts that are camera hardware device agnostic and are applicable to any camera hardware device to control the camera hardware device, wherein the one or more scripts which are camera hardware agnostic is not committed to a particular camera hardware device and are utilized to manipulate or view video received from any type of camera hardware device at the patient's location;

executing the one or more scripts that are applicable to any camera hardware device to control the camera hardware device;

converting the one or more scripts to driver commands for the camera hardware device in the patient's location using the driver determined for the camera hardware device;

communicating the driver commands to the camera hardware device in the patient's location; and executing the driver commands for the camera hardware device in the patient's location to cause the camera hardware device to perform one or more functions.

2. The media of claim 1, wherein the functions comprise one or more of panning the camera hardware device left, panning the camera hardware device right, tilting the camera hardware device up, tilting the camera hardware device down, tilting the camera diagonally up and left, tilting the camera hardware device up and right, tilting the camera hardware device down and left tilting the camera hardware device down and right, zooming the camera hardware device in, zooming the camera hardware device out, muting a local microphone of the camera hardware device, unmuting a local microphone of the camera hardware device, muting a speaker of the camera hardware device, unmuting a speaker of the camera hardware device and setting microphone volumes of the camera hardware device.

3. The media of claim 1, wherein the functions comprise one or more of enabling night vision of the camera hardware device, disabling night vision of the camera hardware device, performing manual focusing of the camera hardware device, changing brightness of the camera hardware and selecting one camera device over another when there are more than one camera hardware devices at the patient's location.

4. The media of claim 1, further comprising
receiving a request to execute one or more scripts to shut down the remote connection from a clinician;
executing one or more shut down scripts that are applicable to any camera hardware device to control the camera hardware device;
converting the one or more shut down scripts to shut down driver commands for the camera hardware device in the patient's location;
communicating the shut down driver commands to the camera hardware device in the patient's location; and
executing the shut down driver commands for the camera hardware device in the patient's location to cause the camera hardware device to perform one or more shut down functions.

5. The media of claim 1, wherein the shut down functions includes facing the camera hardware device away from the patient, turning off speakers and microphones of the camera hardware device and turning off the hardware camera device.

6. One or more computer-readable storage media having computer-executable instructions embodied thereon, that, when executed by a computer device, directly feeds video from a patient location such that it is displayed at a remote clinician location and directly feeds video from the remote clinician location such that it is displayed at a patient location substantially simultaneously, the method comprising:
receiving a request from a clinician to establish contact with a patient at a separate patient location, wherein the request is received from an electronic medical record for the patient while the clinician is accessing the electronic medical record;
receiving identification of a patient location having a first camera hardware device and a first display device;
determining a driver for the first camera hardware device at the patient's location;
receiving identification of the clinician location that is remote from the patient's location having a second camera hardware device and a second display device;
determining the driver for the second camera hardware device at the clinician's location;
connecting with the first and second camera hardware devices and first and second display devices;
receiving one or more script requests to execute one or more scripts that are camera hardware device agnostic and are applicable to any camera hardware device to control at least one of the first and second camera hardware device, wherein the one or more scripts which are camera hardware agnostic is not committed to a particular camera hardware device and are utilized to manipulate or view video received from any type of camera hardware device at one or more of the patient's or clinician's location;
executing at least one of the one or more scripts that are applicable to any camera hardware device to control the first camera hardware device;
executing at least one of the one or more scripts that are applicable to any camera hardware device to control the second camera hardware device;
directly feeding video from the first camera hardware device at the patient's location to the second display device at the clinician's location; and
directly feeding video from the second camera hardware device at the clinician's location to the first display device at the patient's location.

7. The media of claim 6, further comprising:
converting the at least one of the one or more scripts to first driver commands for the first camera hardware device in the patient's location;
communicating the first driver commands to the first camera hardware device in the patient's location; and
executing the first driver commands for the first camera hardware device in the patient's location to cause the first camera hardware device to perform a function.

8. The media of claim 7, further comprising:
converting the at least one of the one or more scripts to second driver commands for the second camera hardware device at the clinician's location;
communicating the second driver commands to the second camera hardware device at the clinician's location; and
executing the second driver commands for the second camera hardware device at the clinician's location to cause the second camera hardware device to perform a function.

9. The media of claim 8, wherein the functions comprise one or more of enabling night vision of the camera hardware device, disabling night vision of the camera hardware device, performing manual focusing of the camera hardware device, changing brightness of the camera hardware and selecting one camera device over another when there are more than one camera hardware devices at the patient's location.

10. The media of claim 8, wherein the functions comprise one or more of panning the camera hardware device left, panning the camera hardware device right, tilting the camera hardware device up, tilting the camera hardware device down, tilting the camera diagonally up and left, tilting the camera hardware device up and right, tilting the camera hardware device down and left tilting the camera hardware device down and right, zooming the camera hardware device in, zooming the camera hardware device out, muting a local microphone of the camera hardware device, unmuting a local microphone of the camera hardware device, muting a speaker of the camera hardware device, unmuting a speaker of the camera hardware device and setting microphone volumes of the camera hardware device.

11. The media of claim 6, further comprising:
directly feeding audio from the first camera hardware device at the patient's location to the second display device at the clinician's location; and
directly feeding audio from the second camera hardware device at the clinician's location to the first display device at the patient's location.

12. The media of claim 11, wherein the video and audio from the first and second camera hardware device is streamed directly from the patient's location to the clinician's location and from the clinician's location to the patient's location without the use of codec or other encoding of the audio and video streams from the first and second camera hardware devices.

13. One or more computer-readable storage media having computer-executable instructions embodied thereon, that, when executed by a computing device, executes driver commands for a first camera hardware device at a patient's location and a second camera hardware device a clinician's location, the method comprising:

receiving a request from a clinician to establish contact with a patient at a separate patient location, wherein the request is received from an electronic medical record for the patient while the clinician is accessing the electronic medical record;

receiving identification of a patient location having a first camera hardware device and clinician location that is remote from the patient location having a second camera hardware device;

determining a first driver for the first camera hardware device at the patient's location and a second driver for the second hardware device at the clinician's location;

connecting with the first and second camera hardware devices;

receiving one or more requests to execute one or more scripts that are camera hardware device agnostic and are applicable to any camera hardware device to control at least one of the first and second camera hardware device, wherein the one or more scripts which are camera hardware agnostic is not committed to a particular camera hardware device and are utilized to manipulate or view video received from any type of camera hardware device at one or more of the patient's or clinician's location;

executing the one or more scripts that are applicable to any camera hardware device to control the first and second camera hardware devices;

converting the one or more scripts to first driver commands for the first camera hardware device at the patient's location and to second driver commands for the second camera hardware device at the clinician's location;

communicating the first driver commands to the first camera hardware device at the patient's location and the second driver commands to the second camera hardware device at the clinician's location; and executing the first driver commands for the first camera hardware device at the patient's location to cause the second camera hardware device to perform one or more functions and the second driver commands for the second camera hardware device at the clinician's location to cause the second camera hardware device to perform one or more functions.

14. The media of claim 13, wherein the functions comprise one or more of panning the camera hardware device left, panning the camera hardware device right, tilting the camera hardware device up, tilting the camera hardware device down, tilting the camera diagonally up and left, tilting the camera hardware device up and right, tilting the camera hardware device down and left tilting the camera hardware device down and right, zooming the camera hardware device in, zooming the camera hardware device out, muting a local microphone of the camera hardware device, unmuting a local microphone of the camera hardware device, muting a speaker of the camera hardware device, unmuting a speaker of the camera hardware device and setting microphone volumes of the camera hardware device.

15. The media of claim 13, wherein the functions comprise one or more of enabling night vision of the camera hardware device, disabling night vision of the camera hardware device, performing manual focusing of the camera hardware device, changing brightness of the camera hardware and selecting one camera device over another when there are more than one camera hardware devices at the patient's location.

16. The media of claim 13, further comprising receiving a request to shut down the remote connection from a clinician;

executing shut down scripts that are applicable to any camera hardware device to control the first and second camera hardware devices;

converting the shut down scripts to shut down driver commands for the first and second camera hardware devices at the patient's location and clinician location;

communicating the shut down driver commands to the first and second camera hardware devices at the patient's location and clinician's location; and executing the shut down driver commands for the first and second camera hardware devices to cause the first and second camera hardware devices to perform one or more shut down functions.

\* \* \* \* \*